(12) United States Patent  (10) Patent No.: US 9,332,995 B2
Russo et al.  (45) Date of Patent: May 10, 2016

(54) BONE-HARVESTING TOOL

(71) Applicants: Scott S. Russo, Grand Rapids, MI (US); Jeremy S. Russo, Grand Rapids, MI (US)

(72) Inventors: Scott S. Russo, Grand Rapids, MI (US); Jeremy S. Russo, Grand Rapids, MI (US)

(73) Assignee: Russo Inventions, LLC, Grand Rapids, MI (US)

( * ) Notice: Subject to any disclaimer, the term of this patent is extended or adjusted under 35 U.S.C. 154(b) by 129 days.

(21) Appl. No.: 14/036,558

(22) Filed: Sep. 25, 2013

(65) Prior Publication Data

US 2014/0088599 A1  Mar. 27, 2014

Related U.S. Application Data

(60) Provisional application No. 61/705,257, filed on Sep. 25, 2012.

(51) Int. Cl.
*A61B 17/14* (2006.01)
*A61B 17/16* (2006.01)

(52) U.S. Cl.
CPC ........... *A61B 17/141* (2013.01); *A61B 17/1635* (2013.01); *A61B 17/1659* (2013.01)

(58) Field of Classification Search
CPC .. A61B 17/14; A61B 17/141; A61B 17/1635; A61B 17/1659
USPC ..................................... 606/79–85
See application file for complete search history.

(56) References Cited

U.S. PATENT DOCUMENTS

| | | | |
|---|---|---|---|
| 3,852,881 A | 12/1974 | Treace | |
| 4,203,444 A | 5/1980 | Bonnell | |
| 4,513,742 A | 4/1985 | Arnegger | |
| 4,733,663 A | 3/1988 | Farley | |
| 5,403,318 A | 4/1995 | Boehringer | |
| 5,507,763 A | 4/1996 | Petersen | |
| 5,569,257 A | 10/1996 | Arnegger | |
| 5,681,337 A | 10/1997 | Bray, Jr. | |
| 5,725,531 A | 3/1998 | Shapiro | |
| 5,857,995 A | 1/1999 | Thomas | |
| 5,925,056 A * | 7/1999 | Thomas | A61B 17/1615 606/170 |
| 6,425,920 B1 | 7/2002 | Hamada | |
| 8,529,568 B2 * | 9/2013 | Bouadi | A61B 17/1604 606/84 |
| 2005/0075642 A1 | 4/2005 | Felt | |
| 2006/0212060 A1 * | 9/2006 | Hacker | A61B 17/320016 606/180 |
| 2008/0208194 A1 | 8/2008 | Bickenbach | |
| 2011/0071572 A1 | 3/2011 | Sixto | |
| 2011/0319899 A1 * | 12/2011 | O'Neil | A61B 17/1659 606/84 |
| 2012/0310113 A1 * | 12/2012 | Giddings | A61B 10/0051 600/570 |

OTHER PUBLICATIONS

Buxton Biomedical, Inc., "Spinal Instruments from Buxton Biomedical," 110 pages.
Buxton Biomedical, Inc., "Talking Back," vol. 1, No. 1, Fall 1994, 4 pages.
Buxton Biomedical, Inc., "Talking Back," vol. 1, No. 2, Winter 1995, 4 pages.

(Continued)

*Primary Examiner* — Christopher Beccia
(74) *Attorney, Agent, or Firm* — Price Heneveld LLP

(57) ABSTRACT

A bone-harvesting tool for use with a manual handle or with an oscillating surgical device. The tool has upper and lower planar surfaces and is symmetrical about a central window that is formed by a pair of elongated facing shaving edges at the lower surface of the tool. Additional sharp shaving edges can optionally be formed in the exterior surface of the tool.

18 Claims, 1 Drawing Sheet

(56) References Cited

OTHER PUBLICATIONS

Buxton Biomedical, Inc., "Talking Back," vol. 1, No. 3, Spring 1995, 4 pages.
Buxton Biomedical, Inc., "Talking Back," vol. 1, No. 4, Winter 1996, 4 pages.
Buxton Biomedical, Inc., "Talking Back," vol. 2, No. 1, Spring 1997, 4 pages.
Buxton Biomedical, Inc., "Talking Back," vol. 2, No. 2, Winter 1998, 4 pages.
Buxton Biomedical, Inc., "Talking Back," vol. 2, No. 3, Spring 1999, 4 pages.
Buxton Biomedical, Inc., "Talking Back," vol. 2, No. 4, Winter 2002, 4 pages.
Buxton Biomedical, Inc., "Talking Back," vol. 3, No. 1, 4 pages.
Buxton Biomedical, Inc., Miscellaneous Product Sheets, 8 pages.
Life Instrument Corp., "Curettes," 13 pages.
Life Instrument Corp., "Elevators & Dissectors," 10 pages.
Life Instrument Corp., "Extra Long Anterior Instrument Set," 1 page.
Life Instrument Corp., "Kits/Cases/Frame/Misc.," 9 pages.
Life Instrument Corp., "Mallets/Tamps," 4 pages.
Life Instrument Corp., "Osteotomes/Gouges," 7 pages.
Life Instrument Corp., "Retractors," 11 pages.
Life Instrument Corp., "Rongeurs," 13 pages.

* cited by examiner

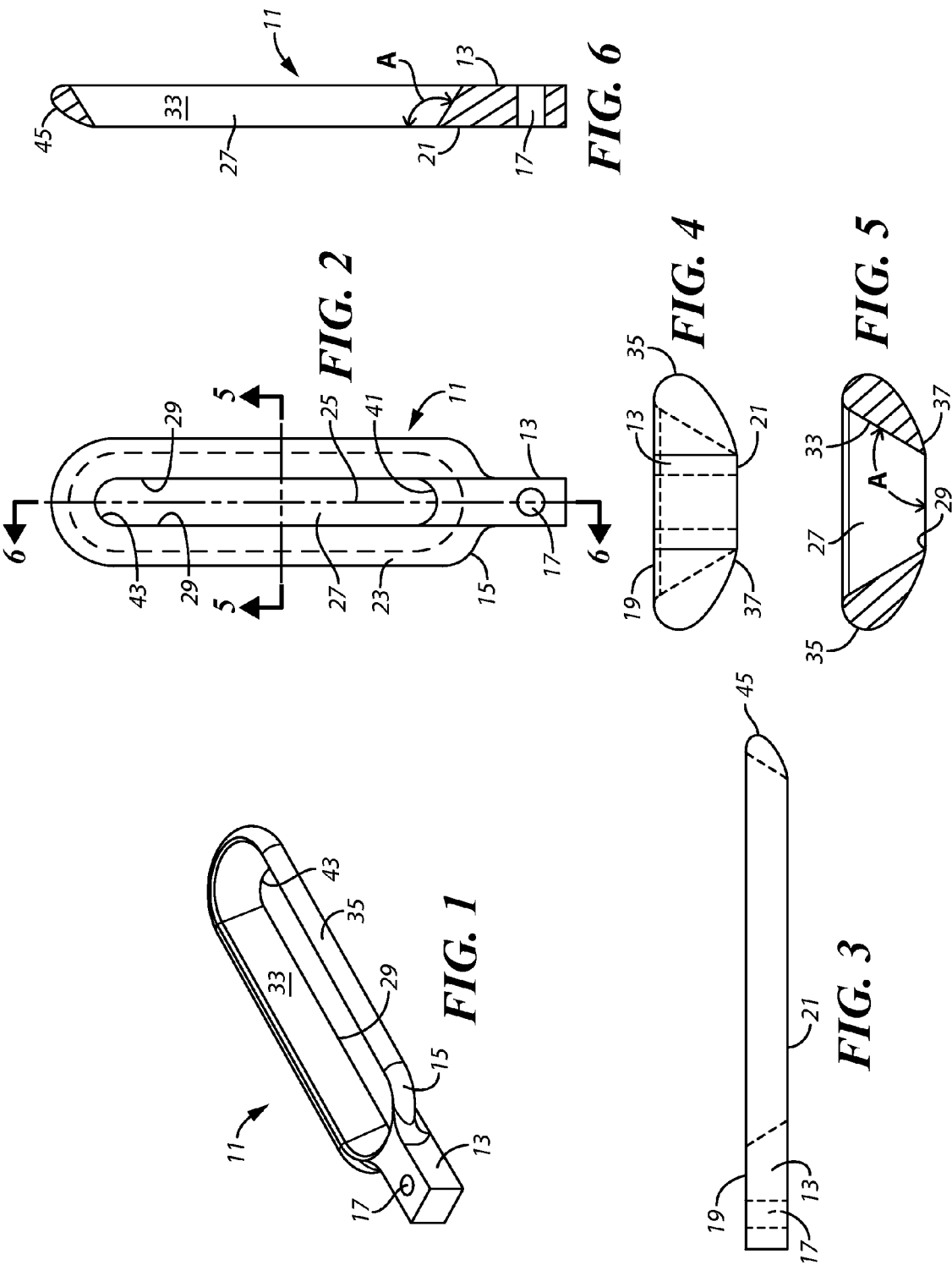

BONE-HARVESTING TOOL

This application claims priority from U.S. Provisional Patent Application No. 61/705,257, filed Sep. 25, 2012, the disclosure of which is incorporated herein by reference.

FIELD OF THE INVENTION

This invention relates generally to a bone-harvesting tool and more particularly to a bone-harvesting tool for attachment to a handle or to an oscillating medical device, which tool is designed to shave and/or contour bone and to permit collection of the shavings.

There are a number of companies in the United States that manufacture and market oscillating medical devices such as oscillating micro surgical saws and surgical drill/burr medical devices. These include Stryker Corporation (who market a line of CORE micro saws), Midas Rex saws, owned by Medtronic, Anspach saws marketed by The Anspach Effect, and the Microaire Surgical Instruments line of micro saws. Blades for these oscillating medical devices are designed with a shank portion that connects to the motor-driven surgical device and a blade portion, the distal end of which generally has a cutting edge that may be straight or arcuate and that usually includes a series of teeth. Although these current saw blades for oscillating saws effectively cut bone and in some versions may remove bone fragments, it would be desirable to be able to have a tool that would shave and harvest bone in a more efficient and effective manner which could be used manually or attached to such a medical device.

SUMMARY OF THE INVENTION

The present invention is directed to a medical tool for harvesting bone that is shaved from a patient's body for autologous graft purposes, as well as for reshaping of critical orthopedic areas in the spine and musculoskeletal system. The tool is a relatively thin metal product which primarily functions via a pair of facing cutting blades that form the partial outline shape of a window in an overall blade portion, which has upper and lower surfaces that preferably lie in parallel planes. These shaving edges are formed with a particular cutting angle that has been found to effectively shave or slice thin slivers of bone from a patient. It is designed for operation with an oscillating medical device, but it can also be used manually by attachment to a suitable handle.

BRIEF DESCRIPTION OF THE DRAWINGS

FIG. 1 is a perspective view showing a shaving tool designed for use with an oscillating medical device which tool embodies various features of the present invention.

FIG. 2 is a top plan view of the shaving tool of FIG. 1.

FIG. 3 is a right-side view of the shaving tool of FIG. 1.

FIG. 4 is a proximal end view of the shaving tool of FIG. 1, enlarged in size.

FIG. 5 is a cross-sectional view taken along line 5-5 of FIG. 2, enlarged in size.

FIG. 6 is cross-sectional view taken along the centerline of the tool, which is line 6-6 of FIG. 2.

DETAILED DESCRIPTION OF THE PREFERRED EMBODIMENTS

Objectives of the invention are embodied in one embodiment of a bone-harvesting tool 11 shown in FIGS. 1-6. The illustrated embodiment is a presently preferred version of a bone-harvesting tool; however, it should be understood that a study of the illustrated tool will bring to mind modifications that one might incorporate, some of which are mentioned hereinafter.

The tool 11 includes a shank portion 13 and a blade portion 15. The shank portion 13 may have any suitable construction that will permit it to be interconnected with a particular manufacturer's oscillating device, such as a micro saw or drill/burrer, or to a suitable handle for use manually by a surgeon. In the illustrated embodiment, the shank portion 13 is square in cross-section and includes a hole 17 that extends completely through the shank between an upper or dorsal surface 19 and a lower or palmar surface 21 of the tool. The hole 17 facilitates attachment to an oscillating medical device or to a manual handle.

As can be seen from FIG. 4, both the dorsal and the palmar surfaces of the tool lie in parallel planes.

The blade portion of the bone-harvesting tool comprises a body 23 which is integral with the shank portion 13 and is generally oval in shape, as can be seen from FIG. 2. The body 23 is elongated and is symmetrical about a centerline 25 of the tool. The centerline 25 bisects a central window 27 which, in the illustrated embodiment, is also of oval shape. The window 27 has a pair of parallel, elongated, straight side edges 29 which are formed as two facing cutting blades. Sidewall surfaces 33 interior of the body that define the window 27 are rectilinear surfaces that are oriented at an open angle A to the planar palmar surface 21 of the tool, as seen in FIG. 5. Angle A is preferably formed to be between about 120° and about 130° and more preferably between about 122° and about 126°.

Outer side surfaces 35 of the body of the blade portion 15 are rectilinear curved surfaces which slope downward and inward from an upper arcuate region, as best seen in FIG. 4, terminating at a lowermost curved region 37 that is substantially tangent to the planar lower surface of the tool. It has been found that shaving edges 29 of this configuration, formed as two facing edges that flank a central window 27, provide an excellent bone-shaving tool 11 that can be effectively used with an oscillating medical device to harvest bone in order to prepare for autologous bone grafting procedures or the like. The tool can also be used manually by attachment to a handle.

The central window 27 has proximal and distal arcuate ends 41, 43 that are essentially semi-circular and interconnect the two elongated side edges 29. The angular A configuration is preferably also maintained throughout the proximal and distal ends of the window 27 as can be seen in FIG. 6.

Likewise, in the illustrated embodiment, the outer surfaces of the body 23, both at its distal end 45 and at the regions where it joins the shank portion 13 at its proximal end, retain an arcuate shape similar to that of the outer side surfaces 35.

The bone-harvesting tool 11 might be about 2.5 mm thick, about 10 mm wide and about 3 cm in length from the distal tip to the proximal end of the shank portion. The oval window might have a width of about 4 mm and a length of about 20 mm. These dimensions would be appropriate for one particular bone-harvesting tool, but of course it would be understood that these dimensions are only illustrative as such a bone-harvesting tool is expected to be produced in varying sizes to meet the needs of particular and different medical procedures.

While the embodiment illustrated in FIG. 1-6 embodies particular features of the invention, it may optionally be modified so as to render the tool 11 even more useful. For example, the exterior surface of the distal tip of the body can be sharpened so that, when attached to an oscillating device, e.g. a surgical drill/burr, it can be used to gouge bone chips from a desired location. Moreover, one or both of the outer side surfaces of the body can be sharpened to also serve as a shaving edge that would permit bone-shaving in another dimension in addition to that provided by the facing shaving edges 29 at the palmar surface.

Likewise, other changes and modification as would be obvious to one having ordinary skill in this art may be made without deviating from the inventive concept that is detailed in the claims appended hereto.

Particular features of the invention are explicitly stated in the claims that follow.

The invention claimed is:

1. A bone-shaving tool, which tool comprises:
   a proximal shank portion configured to be attached to a handle or to a power tool;
   a blade portion configured to shave bone from a patient which extends from said shank portion to a distal end;
   said blade portion comprising a body that includes a central window that extends upward upwardly and outwardly from a substantially planar lower surface at the bottom of the body, said central window being generally aligned with a longitudinal centerline extending between said proximal shank portion and said distal end;
   said window being formed with a pair of substantially parallel elongated side edges which lie at said planar lower surface and form two facing shaving edges; and
   said blade portion is formed of two mirror-image halves which flank said longitudinal centerline; and wherein an upper portion of the central window of the body of the blade portion has both inner and outer smooth and generally oval surfaces around the circumference of the upper central window area, and a lower portion of the central window which is open at the bottom surface of the body of the blade portion also has an inner smooth and generally oval surface around the circumference of the lower central window area.

2. The shaving tool of claim 1 wherein said blade portion is of elongated shape and said window is bisected by said longitudinal centerline.

3. The shaving tool of claim 1 wherein said blade portion has two outer side surfaces which are substantially parallel to said shaving edges of said window.

4. The shaving tool of claim 3, wherein said body has an undersurface which slopes downward and inward from an arcuate upper region to said window shaving edges.

5. The shaving tool of claim 4 wherein said outer side surfaces are shaped to terminate at a lowermost curved region that is substantially tangent to said planar lower surface.

6. The shaving tool of claim 5 wherein each said shaving blade is oriented at an open angle between about 120° and about 130° to said planar lower surface.

7. The shaving tool of claim 6 wherein said blade portion has an interior region that tapers downward and inward and terminates in said window, which window has an oval shape that includes said two facing side shaving edges.

8. The shaving tool of claim 7 wherein said shaving blades are oriented at an open angle between about 122° and about 126°.

9. The shaving tool of claim 3, wherein at least one of the outer side surfaces comprises a shaving edge blade at an upper extent of the blade portion on one side of the central window.

10. The shaving tool of claim 3, wherein each of the outer side surfaces comprise a shaving edge blade at an upper extent of the blade portion body on either side of the central window.

11. The shaving tool of claim 1, wherein said distal end of said blade portion has an arcuate tip configuration and extends between said elongated side edges.

12. A cutting instrument, comprising
   a proximal end portion configured to engage with a handle or a tool;
   a head portion at a distal end portion opposite the proximal end portion and spaced therefrom along a longitudinal axis, wherein the head portion includes opposite outer side surfaces;
   a throughbore of the head portion extending transversely to the longitudinal axis through the head portion that terminates in opposite first and second openings in the head portion; the throughbore forms a central window that extends both upwardly and outwardly from a substantially planar lower surface at the bottom of the head portion;
   a first cutting edge extending along one side of the first opening configured to cut bone or tissue when the first cutting edge is drawn along the bone or tissue; and
   a second cutting edge extending along an opposite side of the first opening configured to cut bone or tissue when the second cutting edge is drawn along the bone or tissue; and wherein an upper portion of the central window of the body of the blade portion has both inner and outer smooth and generally oval surfaces around the circumference of the upper central window, and a lower portion of the central window which is open at the bottom surface of the body of the blade portion also has an inner smooth and generally oval surface around the circumference of the lower central window area.

13. The cutting instrument of claim 12, wherein the first and second cutting edges are oriented to cut adjacent bone or tissue when the instrument is shifted in a single direction.

14. The cutting instrument of claim 12, wherein the first and second cutting edges are oriented such that one of the first and second cutting edges is configured to cut an adjacent tissue or bone when the instrument is shifted in a first direction, and the other of the first and second cutting edges is configured to cut an adjacent tissue or bone when the instrument is shifted in a second direction opposite of the first direction.

15. The cutting instrument of claim 12, further comprising a third cutting edge extending along an outer side surface of the head portion.

16. The cutting instrument of claim 15, further comprising a fourth cutting edge extending along an opposite outer side surface.

17. The cutting instrument of claim 12, wherein the head portion comprises an inner sidewall portion that extends between the first and second openings and forms at least part of the throughbore and the first and second cutting edges.

18. The cutting instrument of claim 12, wherein the first and second openings have different sizes.

* * * * *